United States Patent [19]

Eggensperger et al.

[11] 4,040,977
[45] Aug. 9, 1977

[54] PRESERVATIVE AND DISINFECTANT

[75] Inventors: Heinz Eggensperger, Hamburg; Karl-Heinz Diehl, Norderstedt, both of Germany

[73] Assignee: Sterling Drug Inc., New York, N.Y.

[21] Appl. No.: 673,862

[22] Filed: Apr. 5, 1976

Related U.S. Application Data

[63] Continuation-in-part of Ser. No. 511,643, Oct. 3, 1974, abandoned.

[30] Foreign Application Priority Data

Oct. 16, 1973 Germany .............. 2351821

[51] Int. Cl.² .............. C09K 15/16; A61L 9/00; C02B 3/08
[52] U.S. Cl. .............. 252/401; 21/58; 210/64

[58] Field of Search .............. 210/64; 252/401; 424/302; 260/562 B, 561 HL; 21/58

[56] References Cited

FOREIGN PATENT DOCUMENTS

| | | | |
|---|---|---|---|
| 2,004,647 | 2/1970 | Germany | 252/401 |
| 1,311,371 | 4/1971 | United Kingdom | 252/401 |
| 1,214,523 | 3/1968 | United Kingdom | 252/401 |

*Primary Examiner*—Stephen C. Bentley
*Assistant Examiner*—Donald P. Walsh
*Attorney, Agent, or Firm*—Frederik W. Stonner; B. Woodrow Wyatt

[57] ABSTRACT

The invention relates to preservative and disinfecting compositions for aqueous emulsions, suspensions and solutions which are obtained by reaction in water of a haloacetamide or thiocyanoacetamide or mixture thereof; an alcohol or mixture of alcohols; and formaldehyde.

30 Claims, No Drawings

PRESERVATIVE AND DISINFECTANT

CROSS-REFERENCE TO RELATED APPLICATIONS

This application is a continuation-in-part of copending application Ser. No. 511,643, filed Oct. 3, 1974, now abandoned.

BACKGROUND OF THE INVENTION

1. Field of the Invention

This invention relates to novel preservative and disinfectant compositions for aqueous formulations which are obtained by the reaction in water of substituted acetamides, alcohols and formaldehyde.

2. Description of the Prior Art

The disinfecting and preserving action of various alcohols is known ("Sterilisation, Desinfektion, Konservierung, Chemotherapie", pp. 151-155 and p. 360 by Dr. Wallhäuser and Prof. Dr. H. Schmidt, published by Georg Thieme Verlag, Stuttgart, 1967).

It is also known that mixtures of alcohols and formaldehyde which are known to contain hemiformals, as well as the condensation products produced from formaldehyde and alcohols, for example the O-formal of benzyl alcohol as well as the acetals of alcohols and glycols, including glycol monethers, also are very good disinfecting and preservative agents.

Also, the preserving properties of N-hydroxymethyl-haloacetamides is known, and it is further known that the action of these substances can be enhanced by trishydroxyalkyl-hexahydrotriazine (see German Pat. No. 2,004,647).

SUMMARY OF THE INVENTION

In one aspect of the invention there is provided an aqueous preservative and disinfectant composition comprising acetamide-alcohol-formaldehyde condensation products prepared by reacting in water, in the presence of a basic catalyst in an amount sufficient to catalyze the condensation and for a time and at a temperature sufficient to form the condensation products, (a) an acetamide selected from 2-haloacetamide, thiocyanoacetamide and mixtures of said acetamides; (b) an alcohol selected from saturated alkanols, unsaturated alkanols, cycloalkanols, aralkanols unsubstituted on aryl or substituted on aryl by one or two halo substituents, aroxyalkanols, loweralkoxyalkanols, diethylene glycol mono-lower-alkyl ethers, triethylene glycol, alkanols substituted by one or two substituents selected from bromo and chloro, nitroalkanols, and mixtures of said alcohols; and (c) formaldehyde.

The compositions of the invention exhibit antimicrobial activity and are useful for preserving and disinfecting industrial solutions, emulsions, dispersions and suspensions, such as aqueous paints, cold lubricants, solutions and dispersions of adhesives, cosmetic and pharmaceutical products and other aqueous formulations.

In a second aspect of the invention there is provided a method of preserving and disinfecting aqueous solutions, emulsions, dispersions and suspensions susceptible to deterioration due to microbial contamination which comprises adding to said aqueous solutions, emulsions, dispersions and suspensions an antimicrobial effective amount of a composition obtained as disclosed hereinabove.

DETAILED DESCRIPTION INCLUSIVE OF THE PREFERRED EMBODIMENTS

The compositions of the invention are complex mixtures of condensation products which include 2-halo- and/or thiocyano-substituted N-hydroxymethylacetamides, O-hemiformals, O-bisformals as well as O-N-mixed formals and in which N-hydroxymethyl-2-haloacetamide is present in a form which is stable at low temperatures. The compositions are prepared by heating the appropriate reactants in water in the presence of a basic catalyst at temperatures ranging from about 30° C. to the reflux temperature of the reaction mixture, conveniently 30° to 80° C., with reaction time ranging from about one hour to eight hours. Reaction times and temperatures falling outside these ranges may be employed but do not offer any advantage in the preparation of the compositions of the invention. The reaction is preferably carried out at from 60° to 75° C. for about two to three hours. The basic reagent employed as catalyst in the reaction can be any basic reagent which will catalyze the condensation of the acetamide, alcohol and formaldehyde reactants, as is well understood in the art. The amount of the basic reagent employed must be sufficient to catalyze the condensation of the reactants as is also well understood in the art. Such basic reagents are, for example, alkali metal carbonates and bicarbonates such as potassium and sodium carbonate and potassium and sodium bicarbonate.

The molar ratio of reactants (a), (b) and (c) employed in the reaction is preferably in the range of about 1:(1.6 to 3):(1.9 to 6) although ratios outside this range may be employed. In the foregoing disclosed ratios the molar quantity of (c) is calculated on the basis of the molecular weight of formaldehyde ($CH_2O$; mol. wt. 30.03).

The quantity of water employed generally is such as to provide a composition having the desired concentration contemplated for ultimate use, i.e., for addition to the solutions, suspensions, etc., to be preserved and disinfected. However, greater or lesser quantities of water may be employed, the desired final concentration of the composition then being obtained using conventional techniques, e.g. further dilution with water or, where more concentrated compositions are desired, evaporation of solvent. The solubility characteristics of the compositions can be influenced in a desired manner, as would be obvious to those skilled in the art, by appropriate choice of the alcohol or mixtures of alcohols employed in the reaction. Thus, for example, the employment of a doubly ethoxylated alcohol provides a product that is soluble in the oily as well as in the aqueous phase.

The preservative and disinfectant compositions of the invention usually are marketed as aqueous solutions which may, in order to aid solution, contain additional solvents such as alcohols and glycols. Additional known preservative and disinfectant agents, e.g., those derived from acetamides, alcohols and aldehydes also may be incorporated in the compositions of this invention. Other additives such as perfumes and anticorrosive agents, e.g., benzotriazole, may also be incorporated in the compositions of the invention.

Halo as used herein means bromo, chloro, iodo and fluoro.

Alcohols which are employed in the preparation of the compositions of the invention are as follows:

Saturated alkanols having from one to fourteen carbon atoms, preferably four to eight carbon atoms, which may be arranged in straight or branched chains as illustrated by methanol, ethanol, isopropanol, tert-butanol, pentanol, hexanol, octanol, nonanol and tetradecanol; unsaturated alkanols having from three to fourteen carbon atoms, preferably four to eight carbon atoms, arranged in straight or branched chains illustrated by allyl alcohol, methallyl alcohol, 2,2,3-trimethyl-3-buten-1-ol, 7-octen-1-ol, 1-octen-3-ol, 1-decen-4-ol and 2-tetradecen-1-ol; cycloalkanols having five to seven ring carbon atoms and a total of five to ten carbon atoms as illustrated by cyclopentanol, 2-tert-butyl-5-methylcyclopentanol, 1-ethyl-2-methycyclopentanol, cyclohexanol, 2,2,6-trimethylcyclohexanol, 4-isopropylcyclohexanol, 3,3,5-trimethylcyclohexanol, cycloheptanol, 3,3,5-trimethylcycloheptanol, 1,5-dimethylcycloheptanol; aralkanols having from one to four carbon atoms in the alkanol group which may be arranged in straight or branched chains, preferably phenylalkanols wherein phenyl may be unsubstituted or substituted by one or two halo substitutents as illustrated by benzyl alcohol, α-propylbenzyl alcohol, 3-bromobenzyl alcohol, 4-bromo-3-chlorobenzyl alcohol, 2,6-dichlorobenzyl alcohol, 3,4-dichlorobenzyl alcohol, 2,5-dichlorobenzyl alcohol, 3-iodobenzyl alcohol, phenethyl alcohol, α-ethylphenethyl alcohol, 2-fluoro-α,α-dimethylphenethyl alcohol, 2,4-dichloro-α-methyl phenethyl alcohol, 3-phenylpropyl alcohol, 4-(2-chlorophenyl)butyl alcohol and 3-phenylbutyl alcohol; aroxyalkanols having from two to four carbon atoms in the alkanol group which may be arranged in straight or branched chains, preferably phenoxyalkanols, as illustrated by 2-phenoxyethanol, 1-phenoxy-2-propanol, 3-phenoxypropanol, 2-phenoxy-propanol, 2-phenoxybutanol, 4-phenoxybutanol and 1-phenoxy-2-butanol, lower-alkoxyalkanols wherein alkanol has from two to eight carbon atoms which may be arranged in straight or branched chains and lower-alkoxy has from one to six carbon atoms which may be arranged in straight or branched chains as illustrated by 2-methoxyethanol, 2-ethoxyethanol, 2-butoxyethanol, 3-butoxypropanol, 2-ethoxypropanol, 1-butoxy-2-methyl-2-propanol, 1-isopropoxy-2-propanol, 2-hexyloxy-1-butanol, 5-hexyloxy-1-pentanol, 3-butoxy-2-ethylhexanol, 2-ethoxy-1-hexanol, 2-ethoxyheptanol, 6-methoxy-2-heptanol, 7-methoxy-3-heptanol and 4-methoxy-1-octanol; diethylene glycol mono-lower-alkyl ethers wherein lower-alkyl has from one to six carbon atoms which may be arranged in straight or branched chains as illustrated by 2-(2-ethoxy-ethoxy) ethanol (diethylene glycol monoethyl ether), 2-(2-methoxyethoxy) ethanol (diethylene glycol monomethyl ether), 2-(2-butoxyethoxy) ethanol (diethylene glycol monobutyl ether), 2-(2-hexyloxyethoxy) ethanol (diethylene glycol monohexyl ether), 2-(2-isopentyloxyethoxy) ethanol (diethylene glycol monoisopentyl ether) and 2-(2-pentyloxyethoxy) ethanol (diethylene glycol monopentyl ether); triethylene glycol; alkanols having two to fourteen carbon atoms, preferably two to eight carbon atoms, which may be arranged in straight or branched chains and substituted by one or two substituents selected from bromo and chloro as illustrated by 2-chloroethanol, 3-bromopropanol, 2,3-dichloropropanol, 1-bromo-3-chloro-2-propanol, 1-chloro-2-methyl-2-propanol, 2(3 and 4)-chlorobutanol, 5-bromopentanol, 4-bromo-2,4-dimethylpentanol, 1-chloro-3-pentanol, 6-bromohexanol, 5-chlorohexanol, 7-bromoheptanol, 4,7-dichloroheptanol, 1-chloro-2-heptanol, 6,7-dibromo-2-heptanol, 2-bromooctanol, 9-bromononanol, 1-chloro-2-undecanol and 2-bromotetradecanol; nitroalkanols having two to fourteen carbon atoms, preferably two to eight carbon atoms, which may be arranged in straight or branched chains and wherein the nitro and hydroxyl substituents occur on adjacent carbon atoms as illustrated by 2-nitroethanol, 1-nitro-2-propanol, 2-nitropropanol, 2-methyl-2-nitrobutanol, 1-nitro-2-pentanol, 1-nitro-2-hexanol, 2-nitro-3-hexanol, 3-nitro-4-heptanol, 1-nitro-2-octanol and 5-nitro-4-octanol.

The preparation of the compositions of the invention is illustrated by the following examples without, however, being limited thereto;

EXAMPLE I 0.56 Mole of benzyl alcohol, 0.41 mole of diethylene glycol monobutyl ether and 0.45 mole of 2-chloroacetamide was heated with 1.58 moles of formaldehyde (as paraformaldehyde) and a catalytic amount of potassium carbonate in 135 g. of water at 65° to 75° C. with stirring for 2 hours and the reaction mixture was cooled and filtered from undissolved impurities present in the starting materials.

Following a procedure similar to that described in Example 1 and using molar quantities of reactants disclosed in Examples 2 to 5, further compositions of the invention were obtained.

EXAMPLE 2

0.5 Mole of octanol, 0.5 mole of 2,4-dichlorobenzyl alcohol, 0.45 mole of 2-chloroacetamide and 1.6 moles of formaldehyde (as paraformaldehyde) and a catalytic amount of potassium carbonate.

EXAMPLE 3

0.3 Mole allyl alcohol, 0.31 mole of diethylene glycol monobutyl ether, 0.3 mole of 2-chloroacetamide, 1 mole of formaldehyde (as paraformaldehyde), and a catalytic amount of potassium carbonate.

EXAMPLE 4

0.4 Mole of phenylpropanol, 0.4 mole of 4-chlorobutanol, 0.4 mole of diethylene glycol monobutyl ether, 0.4 mole of 2-chloro-acetamide and 2.05 moles of formaldehyde (as paraformaldehyde) and a catalytic amount of potassium carbonate.

EXAMPLE 5

0.6 Mole of 2-ethylhexanol, 0.4 mole of 2-nitropropanol, 0.6 mole of thiocyanoacetamide, 1.8 moles of formaldehyde (as paraformaldehyde) and a catalytic amount of potassium carbonate.

In Examples 1 to 5 above, the ratio of the acetamide : alcohol : formaldehyde reactants is in the range of 1:(1.7 to 3) : (3 to 5).

EXAMPLE 6

A mixture of chloroacetamide (0.13 mole), triethylene glycol (0.27 m.), paraformaldehyde (0.74 m.) and 0.5 g. potassium carbonate in 25.24 g. of water was heated with stirring at 60°-70° C. for two and one-half hours, cooled to room temperature and filtered.

EXAMPLE 7

A mixture of chloroacetamide (13 g.; 0.14 mole), benzyl alcohol (23 g.; 0.21 mole), triethylene glycol (25 g.; 0.17 mole) and 0.3 g. of potassium carbonate in 24.75 g. of water (permutit softened) was heated to 40°-50° C. and paraformaldehyde (8 g.; 0.27 mole) was added portionwise. The mixture was heated with stirring at 60° to 70° C. for 2 hours, cooled to room temperature and filtered. To the clear yellow solution was added a solution of 0.4 g. perfume (Lab. No. 326), 0.5 g. chloromethylisothiazolone (antibacterial) and 0.05 g. benzotriazole in 5 g. of isopropyl alcohol.

EXAMPLE 8

A mixture of chloroacetamide (12.25 g.; 0.13 mole), triethylene glycol (39.8 g.; 0.27 mole) and 0.5 g. potassium carbonate in water (25.24 g.) was heated to 40°-50° C. and paraformaldehyde (22.21 g.; 0.74 mole) was added portionwise. The mixture was heated with stirring at 50°-60° C. for two hours, cooled to room temperature and filtered.

The compositions of the invention possess surprisingly excellent preservative and disinfecting action, which is superior to that of the hereinabove described known preservative agents, particularly when 2-chloroacetamide and/or thiocyanoacetamide are employed in the reaction which provide these compositions. Thus the product of Example 1 is definitely superior to N-hydroxymethylchloroacetamide and to the hemiformal of benzyl alcohol as shown by comparison tests in which the killing action of the investigated materials was demonstrated in suspension tests as per DGHM (see "Richtlinien fur die Pruefung Chemischer Desinfektionsmittel", 3rd supplemental edition, Gustav Fischer Verlag Stuttgard 1972).

| Suspension Test as per DGHM | | | | | | | | | |
|---|---|---|---|---|---|---|---|---|---|
| | Conc. | Staphylococcus aureus | | Escherichia coli | | Pseudomonas aeruginosa | | Proteus vulgaris | |
| | | − | + | − | + | − | + | − | + |
| N-Hydroxymethylchloroacetamide | 5% | 30′ | | 30′ | | 2.5′ | | 15′ | |
| Product of Example 1 | 5% | 2.5′ | | 15′ | | 2.5′ | | 2.5′ | |
| Product of Example 1 | 0.2% | 1 h | | 1 h | | 1 h | | 1 h | |
| Benzyl alcohol hemiformal | 0.2% | 5 h | | 6 h | | 4 h | | 6 h | |

In the above table, the numbers indicate the killing times in minutes (′) or hours (h).

The superior action of the product of the invention also was established in a preserving test in which the effectiveness of chemical preservative agents with respect to in-can preservation of dye dispersions and latex paints was evaluated. For this purpose, test samples are prepared by addition of the preservative in varying concentrations to unpreserved paint formulations. The test samples are challenged by periodic inoculations with microorganisms. The inoculated test samples are evaluated for surviving microorganisms by means of the streak plate subculture technique. The length of time during which microbial growth is not detectable is used as a relative measure of preservative activity.

In carrying out this test, 50 g. samples of the dispersion dye are added to screw-top jars. The preservative agent to be tested is added to the test samples in its proper use concentration. The concentrations are so chosen that they bracket the average use concentration. A non-preserved dispersion dye serves as the growth control.

Two days following the addition of the preserving agent, the test samples are inoculated with 0.2 ml. of a suspension of the test microorganisms. The titer of the inoculum should be at least $10^6$ microorganisms per ml. The samples are reinoculated at weekly intervals. The streak plates are prepared twice weekly and evaluated for growth after 3 days of incubation at 22° C. If negative results are obtained, the streak plates are incubated an additional two days and then reevaluated. The subculturing is carried out on glucose agar plates. The degree of microbial growth is evaluated semiquantitatively on a scale: −, =, = =, = = =. A = = = reading indicates extensive microbial growth and the end of preservative action.

The inoculum for the foregoing described test was prepared as follows:

Microorganisms, such as Pseudomonas aerug., Proteus sp, Escherichia coli and yeasts, are cultured on the surface of glucose-agar plates. Three days old cultures are rinsed off with physiological saline solution and filtered through glass wool. Molds are cultivated on agar slants and added to the inoculation suspension by means of a platinum-wire loop.

The inoculum suspension contains the following microorganisms (bacteria, yeasts and molds): Pseudomonas aeruginosa; Proteus vulgaris; Klebsiella aerobacter; Escherichia coli; various yeasts; Aspergillus niger; Penicillium glaucum; Mucor; Pullularia pullulans.

A preservative agent is judged to be satisfactory under the conditions specified above, if the test samples remain free of appreciable microbial growth for a period of 6 to 8 weeks. Excellent preservative agents can under these conditions maintain test samples free from microbial growth for 10 or more inoculation cycles.

Freedom from microbial growth was achieved through more than 12 inoculation cycles with the product of Example 1, whereas with a well known preservative agent, based on heterocyclic compounds containing nitrogen and sulfur as heteroatoms, the protection lasted only through 5 inoculation cycles.

The minimum inhibitory concentration (MIC) of the compositions of Examples 6 and 7 against a number of bacterial and fungal organisms was determined. The results, expressed in percent concentration, are listed below:

| | MIC (%) | |
|---|---|---|
| Organism | Example 6 | Example 7 |
| Staphylococcus aureus | 0.05 | 0.05 |
| Escherichia coli | 0.03 | 0.02 |
| Proteus vulgaris | 0.06 | 0.02 |
| Streptococcus fecalis | 0.05 | 0.03 |
| Bacillus subtilis | 0.03 | 0.06 |
| Aspergillus niger | 0.10 | 0.03 |
| Penicillium glaucum | 0.125 | 0.02 |
| Pullularia pullulans | 0.06 | 0.02 |
| Candida albicans | 0.25 | 0.05 |

The minimum cidal concentration against a number of bacterial and fungal organisms was determined using the Minimum Inhibitory Concentration Test. The following is a brief description of the procedure employed: Serial dilutions of the test samples were made in Trypticase Soy Broth. The test organisms were added to the broth:product dilutions. Tubes were incubated at 35° C. for 5 days. All negative tubes were subcultured to observe static effects. The minimum cidal concentration (MCC), expressed in percent, of the composition of Example 8 for each organism was determined to be as follows:

| Organism | MCC (%) |
| --- | --- |
| Salmonella choleraesuis ATCC 10708 | 0.06% |
| Salmonella paratyphi ATCC 9281 | 0.008% |
| Salmonella schottmuelleri ATCC 10719 | 0.06% |
| Enterobacter aerogenes ATCC 13048 | 0.06% |
| Escherichia coli ATCC 11229 | 0.1% |
| Proteus vulgaris ATCC 9920 | 0.06% |
| Pseudomonas aeruginosa ATCC 15442 | 0.05% |
| Klebsiella pneumoniae ATCC 9997 | 0.06% |
| Serratia marcescens ATCC 8195 | 0.06% |
| Staphylococcus aureus ATCC 6538 | 0.1% |
| Streptococcus fecalis ATCC 828 | 0.1% |
| Pseudomonas fluorescens ATCC 13525 | 0.06% |
| Bacillus subtilis ATCC 27328 | 0.05% |
| Saccharomyces cerevisiae (Fleishmans strain) | 0.1% |
| Penicillium variable NRRL 3765 | 0.1% |
| Aspergillus niger ATCC 6275 | 0.2% |
| Aureobasidium pullulans ATCC 9348 | 0.1% |
| Candida albicans ATCC 10231 | 0.06% |
| Bacillus megaterium ATCC 27327 | 0.025% |
| Bacillus lichenformis ATCC 27326 | 0.05% |
| Enterobacter cloacae ATCC 7256 | 0.05% |

The effectiveness of the composition of Example 8 as an in-can paint preservative against bacterial contaminants was demonstrated by a modification of the procedure: "Evaluation of Latex Paint Preservative", F. Buono et al., Journal of Paint Technology, Vol. 45, No. 577 (February, 1973). The test modifications basically consisted of the following:

1. The test agent was evaluated for 6 months rather than 21 days. 2. The test paint samples were inoculated with the challenge organisms three times rather than one time.

3. The test paint samples were monitored by the plate count technique rather than a swab sampling technique.

The following is a decription of the test procedure:

1. At time zero (T-O) 500 ml. aliquots of the test paint formulations were inoculated with a mixed inoculum consisting of Gram-positive and Gram-negative test bacteria to give a final concentration of $1.0 \times 10^7 - 1.0 \times 10^8$ organisms per gram of paint.

2. After designated time intervals, one ml. aliquots of each paint formulation were examined for total bacteria count by plating in AOAC Nutrient agar and for the presence of Gram-negative organisms by streaking onto plates of Nutrient and Mac Conkey's agar. The time intervals were as follows:

Time Zero (T-O), after 2 days (T-2 Days), after 1 week (T-1 week), after one month (T-30 Days) and after two months (T-60 Days).

3. At Time 2 months (T-60 Days) steps 1. and 2. outlined above were repeated, i.e., the test formulations were challenged by the 2nd inoculation and similarly evaluated.

4. At time 4 months (T-120 Days) steps 1. and 2. outlined above were again repeated (Inoculation No. 3).

5. The visiosities of all paint formulations were recorded at Times-T-O, T-60 Days, T-120 Days and T-180 Days. All viscosity levels were determined using a Brookfield Viscometer, Model RVF. Test organisms present in the mixed inoculum were:

Gram-positive Bacteria: *Bacillus licheniformis* ATCC 27326; *Bacillus megaterium* ATCC 27327; *Bacillus subtilis* ATCC 27328.

Gram-negative Bacteria: *Pseudomonas aeruginosa* ATCC 10145; *Enterobacter cloacae* ATCC 7256; (Formally *E. aerogenes*).

The paint types employed were:
Interior Acrylic-Rohm & Haas, No. F22-2
Interior Polyvinyl acetate-Celanese, No. 19660-19
Exterior Acrylic-Celanese, No. 19659-24
Exterior Polyvinyl acetate-Celanese, No. 222

Each of the above paint types were obtained free of all preservatives. Test paint formulations containing 0.3% of the composition of Example 8 were prepared from each of the above-noted paint types. Each paint type, free of preservatives, and each paint type containing 0.05% of phenyl mercuric acetate (PMA), served as controls. A1 paint formulations were stored at 35° C. A test agent is considered effective as an in-can paint preservative if it meets the following criteria:

1. Complete elimination of all detectable bacteria test organisms 30 days after each inoculation.

2. Complete elimination of all Gram-negative test bacteria 7 days after each inoculation and maintenance of this level throughout the duration of the test (or up to subsequent rechallenge).

3. No gross losses in viscosity as compared to the parallel PMA control paint formulation.

The results observed for each of the test formulations treated with 0.3% of the composition of Example 8, and for each of the control formulations, when tested in the foregoing described latex paint preservatives evaluation procedure, were as follows:

Paint formulations containing 0.3% of the composition of Example 8 a. No viable bacteria of any type were detected 30 days after each of the three inoculations;

b. No viable Gram-negative organisms were detected 48 hours after each of the three inoculations; and c. No detectable viscosity losses were observed during the duration of the test (6 months).

Paint formulations containing 0.05% of PMA a. No viable bacteria of any type were detected 30 days after each of the three inoculatons in 3 of the 4 paint formulations;

b. No viable Gram-negative organisms were detected 48 hours after each of the three inoculations; and c. No detectable viscosity losses were observed during the duration of the test (6 months).

Paint formulations containing no preservatives a. In all formulations, surviving bacteria were detected 30 days after each of the three inoculations;

b. For all formulations, no Gram-negative organisms were detected after the first inoculation, and Gram-negative organisms were found to survive 48 hours after the second and third inoculation; and c. No viscosity changes were detected in any of the formulations after 2 months; slight viscosity losses were detected in 2 of the 4 formulations after 4 months, and slight to moderate viscosity losses were detected in 3 of the 4 formulations after 6 months.

We claim:

1. An aqueous preservative and disinfectant composition comprising acetamide-alcohol-formaldehyde condensation products prepared by reacting in water, in the presence of a basic catalyst in an amount sufficient to catalyze the condensation and for a time and at a temperature sufficient to form the condensation products, (a) an acetamide selected from 2-haloacetamide, thiocyanoacetamide and mixtures of said acetamides; (b) an alcohol selected from saturated alkanols, unsaturated alkanols, cycloalkanols, aralkanols unsubstituted on aryl or substituted on aryl by one or two halo substituents, aroxyalkanols, lower-alkoxyalkanols, diethylene glycol mono-lower-alkyl ethers, triethylene glycol, alkanols substituted by one or two substituents selected from bromo and chloro, nitroalkanols, and mixtures of said alcohols; and (c) formaldehyde.

2. A composition according to claim 1 wherein (b) is selected from saturated alkanols, unsaturated alkanols, phenylalkanols unsubstituted on phenyl or substituted on phenyl by one or two halo substituents, diethylene glycol mono-lower-alkyl ethers, triethylene glycol, alkanols substituted by a bromo or chloro substituent, nitroalkanols, and mixtures of said alcohols.

3. A composition according to claim 2 wherein (a), (b) and (c) are reacted in a molar ratio of about 1 : (1.6 to 3) : (1.9 to 6).

4. A composition according to claim 3 wherein (a) is 2-chloroacetamide, thiocyanoacetamide or mixtures thereof.

5. A composition according to claim 4 wherein (a) is 2-chloroacetamide and (b) is a mixture of benzyl alcohol and triethylene glycol.

6. A composition according to claim 4 wherein (a) is 2-chloroacetamide; and (b) is triethylene glycol.

7. A composition according to claim 1 wherein (b) is selected from saturated alkanols, unsaturated alkanols, cycloalkanols, aralkanols unsubstituted on aryl or substituted on aryl by one or two halo substituents, aroxyalkanols, lower-alkoxyalkanols, diethylene glycol mono-lower-alkyl ethers, alkanols substituted by one or two substituents selected from bromo and chloro, nitroalkanols, and mixtures of said alcohols.

8. A composition according to claim 7 wherein (b) is selected from saturated alkanols, unsaturated alkanols, phenylalkanols unsubstituted on phenyl or substituted on phenyl by one or two halo substituents; diethylene glycol mono-lower-alkyl ethers, alkanols substituted by a bromo or chloro substituent, nitroalkanols, and mixtures of said alcohols.

9. A composition according to claim 8 wherein (a), (b) and (c) are reacted in a molar ratio of about 1 : (1.7 to 3) : (3 to 5).

10. A composition according to claim 9 wherein (a) is 2-chloroacetamide, thiocyanoacetamide or mixtures thereof.

11. A composition according to claim 10 wherein (a) is 2-chloroacetamide; and (b) is a mixture of benzyl alcohol and diethylene glycol monobutyl ether.

12. A composition according to claim 10 wherein (a) is 2-chloroacetamide; and (b) is a mixture of octanol and 2,4-dichlorobenzyl alcohol.

13. A composition according to claim 10 wherein (a) is 2-chloroacetamide; and (b) is a mixture of allyl alcohol and diethylene glycol monobutyl ether.

14. A composition according to claim 10 wherein (a) is 2-chloroacetamide; and (b) is a mixture of phenylpropanol, 4-chlorobutanol and diethylene glycol monobutyl ether.

15. A composition according to claim 10 wherein (a) is thiocyanoacetamide; and (b) is a mixture of 2-ethylhexanol and 2-nitropropanol.

16. A method for preserving and disinfecting aqueous solutions, emulsions, dispersions and suspensions susceptible to deterioration due to microbial contamination which comprises adding to said aqueous solutions, emulsions, dispersions and suspensions an antimicrobial effective amount of a composition according to claim 1.

17. A method according to claim 16 wherein (b) is selected from saturated alkanols, unsaturated alkanols, phenylalkanols unsubstituted on phenyl or substituted on phenyl by one or two halo substituents, diethylene glycol mono-lower-alkyl ethers, triethylene glycol, alkanols substituted by a bromo or chloro substituent, nitroalkanols, and mixtures of said alcohols.

18. A method according to claim 17 wherein (a), (b) and (c) are reacted in a molar ratio of about 1 : (1.6 to 3) : (1.9 to 6).

19. A method according to claim 18 wherein (a) is 2-chloroacetamide, thiocyanoacetamide or mixtures thereof.

20. A method according to claim 19 wherein (a) is 2-chloroacetamide; and (b) is a mixture of benzyl alcohol and triethylene glycol.

21. A method according to claim 19 wherein (a) is 2-chloroacetamide; and (b) is triethylene glycol.

22. A method according to claim 16 wherein (b) is selected from saturated alkanols, unsaturated alkanols, cycloalkanols, aralkanols unsubstituted on aryl or substituted on aryl by one or two halo substituents, aroxyalkanols, lower-alkoxyalkanols, diethylene glycol mono-lower-alkyl ethers, alkanols substituted by one or two substituents selected from bromo and chloro, nitroalkanols, and mixtures of said alcohols.

23. A method according to claim 22 wherein (b) is selected from saturated alkanols, unsaturated alkanols, phenylalkanols unsubstituted on phenyl or substituted on phenyl by one or two halo substituents, diethylene glycol mono-lower-alkyl ethers, alkanols substituted by a bromo or chloro substituent, nitroalkanols, and mixtures of said alcohols.

24. A method according to claim 23 wherein (a), (b) and (c) are reacted in a molar ratio of about 1 : (1.7 to 3) : (3 to 5).

25. A method according to claim 24 wherein (a) is 2-chloroacetamide, thiocyanoacetamide or mixtures thereof.

26. A method according to claim 25 wherein (a) is 2-chloroacetamide; and (b) is a mixture of benzyl alcohol and diethylene glycol monobutyl ether.

27. A method according to claim 25 wherein (a) is 2-chloroacetamide; and (b) is a mixture of octanol and 2,4-dichlorobenzyl alcohol.

28. A method according to claim 25 wherein (a) is 2-chloroacetamide; and (b) is a mixture of allyl alcohol and diethylene glycol monobutyl ether.

29. A method according to claim 25 wherein (a) is 2-chloroacetamide; and (b) is a mixture of phenylpropanol, 4-chlorobutanol and diethylene glycol monobutyl ether.

30. A method according to claim 25 wherein (a) is thiocyanoacetamide; and (b) is a mixture of 2-ethylhexanol and 2-nitropropanol.

* * * * *